US008697681B2

(12) United States Patent
Oka

(10) Patent No.: US 8,697,681 B2
(45) Date of Patent: Apr. 15, 2014

(54) METHOD FOR PREDICTION OF THERAPEUTIC EFFECT OF CHEMOTHERAPY EMPLOYING EXPRESSION LEVEL OF DIHYDROPYRIMIDINE DEHYDROGENASE GENE AS MEASURE

(75) Inventor: Toshinori Oka, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/321,202

(22) PCT Filed: May 21, 2010

(86) PCT No.: PCT/JP2010/058597
§ 371 (c)(1),
(2), (4) Date: Nov. 18, 2011

(87) PCT Pub. No.: WO2010/134588
PCT Pub. Date: Nov. 25, 2010

(65) Prior Publication Data
US 2012/0156310 A1 Jun. 21, 2012

(30) Foreign Application Priority Data
May 22, 2009 (JP) ................................. 2009-124241

(51) Int. Cl.
A61K 31/555 (2006.01)
A61K 31/505 (2006.01)
A61K 31/34 (2006.01)
A61K 31/28 (2006.01)

(52) U.S. Cl.
USPC ............ 514/184; 514/274; 514/461; 514/492

(58) Field of Classification Search
USPC .................................. 514/184, 274, 461, 492
See application file for complete search history.

(56) References Cited

PUBLICATIONS

Yonemura et al., "Effect of intraperitoneal chemotherapy on experimental peritoneal dissemination of gastric cancer", Gan to Kagaku Ryoho (Japanese Journal of Cancer and Chemotherapy), vol. 32, No. 11, pp. 1635-1639 (see enclosed abstract).*
Ooyama et al., "Gene expression analysis using human cancer xenografts to identify novel predictive marker genes for efficacy of 5-fluorouracil-based drugs", Cancer Science, vol. 97, No. 6, pp. 510-522 (2006).*
Yonemura et al., "Effect of Intraperitoneal chemotherapy on experimental peritoneal dissemination of gastric cancer", Gan to Kagaku Ryoho (Japanese Journal of Cancer and Chemotherapy), vol. 32, No. 11, pp. 1635-1639 (2005). see enclosed abstract.*
Wasaburo Koizumi et al., "S-1 plus cisplatin versus S-1 alone for the first-line treatment of advaned gastric cancer (SPIRITS trial): a phase III trial", Lancet Oncology, 2008, vol. 9, pp. 215-221.
Masakazu Fukushima, "Current Progress of Dihydropyrimidine Dehydrogenase (DPD)-Inhibitory Fluoropyrimidines which Target Tumoral DPD to Potentiate the Antitumor Activity of 5-Fluorouracil", Biotherapy, 2002, vol. 16, No. 4, pp. 306-313.
Hidekazu Kuramochi et al, "High intratumoral dihydropyrimidine dehydrogenase mRNA levels in pancreatic cancer associated with a high rate of response to S-1", Cancer Chemotherapy and Pharmacology, 2008, vol. 63, No. 1, pp. 85-89.
Takeshi Yamada et al., "Orotate Phosphoribosyl Transferase (OPRT), Dihydropyrimidine Dehydrogenase (DPD), Thymidylate Synthase (TS)", Japanese Journal of Cancer and Chemotherapy, 2006, vol. 33, No. 6, pp. 789-793.
Yoichiro Ishikawa et al., "Dihydropyrimidine Dehydrogenase Activity and Messenger RNA Level May be Related to the Antitumor Effect of 5-Fluorouracil on Human Tumor Xenografts in Nude Mice", Clinical Cancer Research, 1999, vol. 5, pp. 883-889.
Kazuhiro Yoshida et al., "Challenge for a better combination with basic evidence", International Journal of Clinical Oncology, 2008, vol. 13, No. 3, pp. 212-219.
Heinz-Joseph Lenz et al., Extended Safety and Efficacy Data on S-1 plus Cisplatin in Patients with Untreated, Advanced Gastric Carcinoma in a Multicenter Phase II Study, Cancer, 2007, vol. 109, No. 1, pp. 33-40.
Jaffer A. Ajani et al., "Multicenter Phase II Trial of S-1 Plus Cisplatin in Patients with Untreated Advanced Gastric or Gastroesophageal Junction Adenocarcinoma", Journal of Clinical Oncology, 2006, vol. 24, No. 4, pp. 663-667.
Wataru Ichikawa, Prediction of clinical outcome of fluoropyrimidine-based chemotherapy for gastric cancer patients, in terms of hte 5-fluorouracil metabolic pathway, Gastric Cancer, 2006, vol. 9, No. 3, pp. 145-155.
Wasaburo Koizumi et al., Impacts of fluorouracil-metabolizing enzymes on the outcomes of patients treated with S-1 alone or S-1 plus cislpatin for first-line treatment of advanced gastric cancer, International Journal of Cancer, Jan. 1, 2010, vol. 126, No. 1, pp. 162-170.
Rudolf Napieralski et al., Combined GADD45A and thymidine phoshorylase expression levels predict response and survival of neoadjuvant-treated gastric cancer patients, Clinical Cancer Research, 2005, vol. 11, No. 8, pp. 3025-3031.
Akio Ooyama et al., Gene expression analysis using human cancer xenografts to identify novel predictive marker genes for the efficacy of 5-fluorouracil-based drug, Cancer Science, 2006, vol. 97, No. 6, pp. 510-522.
Masaya Takizawa et al., In vitro sensitivity to platinum-derived drugs is associated with expression of thymidylate synthase and dihydropyrimidine dehydrogenase in human lung cancer, Oncology Reports, 2006, vol. 15, No. 6, pp. 1533-1539.
Extended European Search Report dated Jan. 3, 2013 for the corresponding European Patent Application No. 10777820.1.

* cited by examiner

Primary Examiner — Kevin E Weddington
(74) Attorney, Agent, or Firm — Rothwell, Figg, Ernst & Manbeck, P.C.

(57) ABSTRACT

The present invention provides an antitumor agent comprising cisplatin and a combination drug of tegafur/gimeracil/oteracil potassium that ensures an excellent life-prolongation effect in advanced gastric cancer patients that is superior to that of the standard therapy in Europe and the U.S. using an agent that contains 5-FU and does not contain a dihydropyrimidine dehydrogenase inhibitor, by way of selecting the patients based on dihydropyrimidine dehydrogenase.

6 Claims, No Drawings

METHOD FOR PREDICTION OF THERAPEUTIC EFFECT OF CHEMOTHERAPY EMPLOYING EXPRESSION LEVEL OF DIHYDROPYRIMIDINE DEHYDROGENASE GENE AS MEASURE

CROSS REFERENCE TO RELATED APPLICATION

This application is a 35 U.S.C. 371 National Phase Entry Application from PCT/JP2010/058597, filed May 21, 2010, which claims the benefit of Japanese Patent Application No. 2009-124241 filed on May 22, 2009, the disclosure of which is incorporated herein in its entirety by reference.

TECHNICAL FIELD

The present invention relates to a method for predicting a therapeutic effect of combination chemotherapy with cisplatin and a combination drug of tegafur/gimeracil/oteracil potassium; an antitumor agent to be administered to a patient who is likely to respond to the combination chemotherapy and thereby has a significantly-increased survival advantage; a primer pair; and a kit.

BACKGROUND ART

Domestically and internationally, antitumor agents including 5-fluorouracil (hereinafter referred to as 5-FU), cisplatin, irinotecan, docetaxel, a combination drug of tegafur/uracil (product name: UFT®), a combination drug of tegafur/gimeracil/oteracil potassium (product name: TS-1®, hereinafter, a preparation comprising tegafur/gimeracil/oteracil potassium at a molar ratio of 1:0.4:1 is referred to as TS-1) are adopted in clinical chemotherapies to treat advanced gastric cancers both solely or in a combination of two or more. Although combination chemotherapy of 5-FU and cisplatin is used as a standard therapy in Europe and the U.S., its life-prolongation effect is still not fully satisfactory. Therefore, combination chemotherapy of TS-1 and cisplatin is attracting attention with the expectation that it can promise a superior life-prolongation effect (Non-patent Literature 1 and 2).

CITATION LIST

Non-Patent Literature

[Non-patent Literature 1] Cancer 2007; 109:33-40.
[Non-patent Literature 2] J. Clin. Oncol 2006; 24:663-667.

SUMMARY OF INVENTION

Technical Problem

An object of the present invention is to provide combination chemotherapy that exhibits a therapeutic effect (in particular, life-prolongation effect) in advanced gastric cancer patients superior to that of the standard therapy in Europe and the U.S., using an agent that contains 5-FU (such as combination chemotherapy of 5-FU and cisplatin) and does not contain a dihydropyrimidine dehydrogenase inhibitor.

Solution to Problem

The inventors of the present invention conducted extensive research on chemotherapies for advanced gastric cancers, and found that the combination chemotherapy with cisplatin and a combination drug of tegafur/gimeracil/oteracil potassium exhibits a superior life-prolongation effect in the patients having high expression levels (amount of mRNA or enzyme) of dihydropyrimidine dehydrogenase (may be hereinafter referred to as DPD) to the standard therapy in Europe and the U.S. using an agent that contains 5-FU (such as combination chemotherapy of 5-FU and cisplatin) and does not contain a dihydropyrimidine dehydrogenase inhibitor. With this finding, the inventors completed the present invention. The dihydropyrimidine dehydrogenase is a' degradation enzyme of 5-FU, and is hitherto known as a factor for defining the therapeutic effect of 5-FU. However, it is known that the dihydropyrimidine dehydrogenase does not serve as a factor for defining the therapeutic effect of TS-1, because TS-1 contains gimeracil, which is a dihydropyrimidine dehydrogenase inhibitor (for example, see Int. J. Cancer: 119, 1927-1933 (2006)). Moreover, it was completely unknown that the amount of expression product (mRNA, enzyme) of dihydropyrimidine dehydrogenase can be used as an index for predicting a patient who highly responds to the combination chemotherapy with cisplatin and a combination drug of tegafur/gimeracil/oteracil potassium and thereby has a significantly-increased survival advantage, compared to the standard therapy in Europe and the U.S. using an agent that contains 5-FU (such as a combination chemotherapy of 5-FU and cisplatin) and does not contain a dihydropyrimidine dehydrogenase inhibitor.

Specifically, the present invention provides the following methods for predicting a therapeutic effect of combination chemotherapy with cisplatin and a combination drug of tegafur/gimeracil/oteracil potassium; an antitumor agent; primer pairs; and kits.

[Item 1]

A method for predicting a therapeutic effect of combination chemotherapy with cisplatin and a combination drug of tegafur/gimeracil/oteracil potassium with respect to gastric cancer patients, the method comprising the steps of:

(1) measuring an expression level of dihydropyrimidine dehydrogenase gene in a biological sample, which is obtained from a patient and is likely to contain cancer cells; and (2) predicting that the patient is likely to sufficiently respond to the combination chemotherapy when the expression level measured in Step (1) is higher than a corresponding predetermined cut-off point.

[Item 2]

The method according to Item 1, wherein the molar ratio of respective active ingredients in the combination drug of tegafur/gimeracil/oteracil potassium, i.e., the ratio of tegafur:gimeracil:oteracil potassium, is 1:0.4:1.

[Item 3]

An antitumor agent comprising cisplatin and a combination drug of tegafur/gimeracil/oteracil potassium, characterized by performing the combination chemotherapy with respect to a cancer patient assumed to sufficiently respond to the combination chemotherapy in accordance with a result of the method of Item 1 or 2.

[Item 4]

A therapeutic method for gastric cancer, characterized by performing the combination chemotherapy with respect to a cancer patient assumed to sufficiently respond to the combination chemotherapy in accordance with a result of the method of Item 1 or 2.

[Item 5]

Use of an antitumor agent comprising cisplatin and a combination drug of tegafur/gimeracil/oteracil potassium to per-form the combination chemotherapy with respect to a cancer patient assumed to sufficiently respond to the combination chemotherapy in accordance with a result of the method of Item 1 or 2.

[Item 6]

A primer pair for measuring an expression level of dihydropyrimidine dehydrogenase, the primer pair comprising a forward primer of SEQ ID NO: 1 and a reverse primer of SEQ ID NO: 2; or comprising a forward primer of SEQ ID NO: 7 and a reverse primer of SEQ ID NO: 8.

[Item 7]

The primer pair according to Item 6 for use in prediction of a therapeutic effect of combination chemotherapy comprising a combination drug of tegafur/gimeracil/oteracil potassium.

[Item 8]

The primer pair according to Item 7 for use in prediction of a therapeutic effect of combination chemotherapy with cisplatin and a combination drug of tegafur/gimeracil/oteracil potassium with respect to gastric cancer patients.

[Item 9]

A kit for predicting a therapeutic effect of combination chemotherapy comprising a combination drug of tegafur/gimeracil/oteracil potassium, the kit comprising a primer pair for measuring an expression level of dihydropyrimidine dehydrogenase, the primer pair comprising a forward primer of SEQ ID NO: 1 and a reverse primer of SEQ ID NO: 2; or comprising a forward primer of SEQ ID NO: 7 and a reverse primer of SEQ ID NO: 8.

[Item 10]

The kit according to Item 9 for use in prediction of a therapeutic effect of combination chemotherapy with cisplatin and a combination drug of tegafur/gimeracil/oteracil potassium with respect to gastric cancer patients.

[Item 11]

The kit according to Item 10, further comprising a probe of SEQ ID NO: 3 or SEQ ID NO: 9.

Effect of Invention

The prediction method of the present invention enables selection of effective combination chemotherapy that ensures a therapeutic effect (in particular, life-prolongation effect) in gastric cancer patients that is superior to that of the standard therapy in Europe and the U.S. using an agent that contains 5-FU and does not contain a dihydropyrimidine dehydrogenase inhibitor. More specifically, the present invention makes it possible to accurately provide effective combination chemotherapy that has a superior therapeutic effect (in particular, life-prolongation effect) in gastric cancer patients, thereby allowing the patients to avoid unnecessary chemotherapies. Therefore, the present invention also has an advantage in terms of medical care expenses.

DESCRIPTION OF EMBODIMENTS

The prediction method of the present invention predicts those patients who are likely to sufficiently respond to combination chemotherapy with cisplatin and a combination drug of tegafur/gimeracil/oteracil potassium (in particular, in terms of life prolongation), based on the expression level of dihydropyrimidine dehydrogenase gene in patients.

In the present invention, "combination chemotherapy with cisplatin and a combination drug of tegafur/gimeracil/oteracil potassium" means chemotherapy in which both antitumor agents, i.e., cisplatin and a combination drug of tegafur/gimeracil/oteracil potassium, are administered in combination. When cisplatin and the combination drug are administered in combination, they may be administered simultaneously, or separately at a fixed interval.

In the present invention, "sufficiently respond to the combination chemotherapy" indicates a condition in which a patient responds to the combination chemotherapy to a greater extent than that achieved with a standard therapy containing 5-FU, which is used in, for example, Europe and the U.S. (e.g., combination chemotherapy with 5-FU and cisplatin). Whether such a greater condition is shown can be determined by confirming whether the expression level of dihydropyrimidine dehydrogenase gene is not less than a cut-off point. The expression level of dihydropyrimidine dehydrogenase gene that is not less than a cut-off point is regarded as ensuring a sufficient therapeutic effect of the combination chemotherapy.

The therapeutic effect in the present invention can be determined as a life-prolongation effect or a tumor-shrinking effect. Preferably, the therapeutic effect is determined as a life-prolongation effect. The life-prolongation effect can be evaluated by median survival time (the longer the survival time, the greater the life-prolongation effect), 1-year survival rate and 2-year survival rate (the larger the rate, the greater the life-prolongation effect), hazard (mortality rate at a certain moment), etc.

Tegafur (generic name, chemical name: 5-fluoro-1-(2-tetrahydrofuryl)-2,4-(1H, 3H)-pyrimidinedione), an active ingredient in the present invention, is a known compound; and is a drug that is activated in vivo to release 5-FU, which is a substance responsible for antitumor activity. Tegafur can be produced according to known methods such as, for example, the method disclosed in Japanese Examined Patent Publication No. S49-10510.

Gimeracil (generic name, chemical name: 2,4-dihydroxy-5-chloropyridine), an active ingredient in the present invention, is also a known compound. Although gimeracil itself does not exhibit any antitumor activity, it can inhibit metabolic inactivation of 5-FU in vivo, thereby potentiating the antitumor effect.

Oteracil potassium (generic name, chemical name: monopotassium 1,2,3,4-tetrahydro-2,4-dioxo-1,3,5-triazine-6-carboxylate), an active ingredient in the present invention, is also a known compound. Although oteracil potassium itself does not exhibit any antitumor activity, it is chiefly distributed in the gastrointestinal tract, where it inhibits the activation of 5-FU, thereby preventing gastrointestinal tract disorders.

Cisplatin (generic name, chemical name: (SP-4-2) Diamminedichloroplatinum), an active ingredient in the present invention, is a known platinum complex compound, and is known to exhibit an antitumor effect due to DNA synthesis inhibitory action. Cisplatin can be produced according to known methods. Further, commercially available pharmaceutical products, such as Briplatin (registered trademark, produced by Bristol-Myers Co.), may be used.

The proportion of tegafur, gimeracil and oteracil potassium that are administered in the present invention is not particularly limited as long as the purpose of each ingredient is achieved. For example, the proportion of tegafur, gimeracil and oteracil potassium may be within the same range as that in the known combination drug disclosed in U.S. Pat. No. 2,614,164. The proportion is usually such that, per mole of tegafur, gimeracil is used in a proportion of about 0.1 to about 5 moles and preferably about 0.2 to about 1.5 moles, and oteracil potassium is used in a proportion of about 0.1 to about 5 moles and preferably about 0.2 to about 2 moles. It is particularly preferred that the molar ratio of tegafur:gimeracil:oteracil potassium is 1:0.4:1.

The proportion of cisplatin that is administered in the present invention is not particularly limited as long as an antitumor effect is attained. For example, it is usually such that, per mole of tegafur, cisplatin is used in a proportion of about 0.01 to about 5.0 moles, preferably about 0.1 to about 2.0 moles, and more preferably about 0.2 to about 1.5 moles as a daily dose.

The dose of each active ingredient in the present invention is suitably selected according to conditions such as dose regimen, age and sex of a patient, stage of disease, presence or absence of metastasis, medical history, and presence or absence of other antitumor agents. The pharmaceutical preparations of the present invention are preferably given in an amount using the following range as a standard: the amount of tegafur is about 0.1 to about 100 mg/kg/day, preferably about 0.2 to about 40 mg/kg/day, and more preferably about 0.5 to about 20 mg/kg/day; the amount of gimeracil is about 0.02 to about 30 mg/kg/day, preferably about 0.05 to about 12 mg/kg/day, and more preferably about 0.1 to about 6 mg/kg/day; the amount of oteracil potassium is about 0.1 to about 100 mg/kg/day, preferably about 0.2 to about 40 mg/kg/day, and more preferably about 0.5 to about 20 mg/kg/day; and the amount of cisplatin is about 0.08 to about 200 mg/kg/day, preferably about 0.15 to about 80 mg/kg/day, and more preferably about 0.4 to about 40 mg/kg/day. Further, each active ingredient is administered in a single dose or multiple divided doses per day. The active ingredients are administered simultaneously or separately at intervals, and the order of administration thereof is not particularly limited.

In the present invention, tegafur, gimeracil, and oteracil potassium are provided as a combination preparation formulated into one dosage form. Furthermore, in the present invention, cisplatin may be formulated alone to form a single active ingredient preparation, or formulated in combination with tegafur, gimeracil, and oteracil potassium into one dosage form to form a combination preparation. The tegafur/gimeracil/oteracil potassium preparation and the cisplatin preparation are preferably provided in separately formulated dosage forms.

As long as the active ingredients are administered in combination, each of the above preparations may be individually produced, packed, and distributed, or all or a part of the preparations may be produced, packed, and distributed as a single package (kit formulation) suitable for administering in combination.

The dosage form of the preparations of the present invention is not particularly limited, and specific examples thereof include oral preparations (such as tablets, coated tablets, powders, granules, capsules, and fluids), injections, suppositories, patches, ointments, and the like. When the active ingredients of the present invention are formulated into a plurality of dosage forms, the preparations may be presented in different dosage forms, or in the same dosage form. For example, the combination drug of tegafur/gimeracil/oteracil potassium is preferably an oral preparation, and the preparation containing cisplatin is preferably an injection.

The preparations of the present invention are produced using a pharmacologically acceptable carrier by formulation methods that are commonly known in each dosage form. Examples of the carrier include those that are widely used in common drugs, such as excipients, binders, disintegrators, lubricants, diluents, solubilizing agents, suspending agents, tonicity adjusting agents, pH adjusters, buffers, stabilizers, colorants, sweetening agents, and flavoring agents.

Examples of excipients include lactose, saccharose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerol, sodium alginate, gum arabic, mixtures thereof, and the like.

Examples of lubricants include purified talc, stearic acid salts, borax, polyethylene glycol, mixtures thereof, and the like.

Examples of binders include simple syrups, glucose solutions, starch solutions, gelatin solutions, polyvinyl alcohol, polyvinyl ether, polyvinylpyrrolidone, carboxymethylcellulose, shellac, methylcellulose, ethylcellulose, water, ethanol, potassium phosphate, mixtures thereof, and the like.

Examples of disintegrators include dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, lactose, mixtures thereof, and the like.

Examples of diluents include water, ethyl alcohol, macrogol, propylene glycol, ethoxylated isostearyl alcohol, polyoxylated isostearyl alcohol, polyoxyethylene sorbitan fatty acid esters, mixtures thereof, and the like.

Examples of stabilizers include sodium pyrosulfite, ethylene diamine tetraacetic acid, thioglycolic acid, thiolactic acid, mixtures thereof, and the like.

Examples of tonicity adjusting agents include sodium chloride, boric acid, glucose, glycerol, mixtures thereof, and the like.

Examples of pH-adjusters and buffers include sodium citrate, citric acid, sodium acetate, sodium phosphate, mixtures thereof, and the like.

Examples of soothing agents include procaine hydrochloride, lidocaine hydrochloride, mixtures thereof, and the like.

Examples of colorants include titanium oxide, iron oxide, and the like.

Examples of sweetening/flavoring agents include saccharose, orange peel, citric acid, tartaric acid, and the like.

Examples of solubilizing agents include polyethylene glycol, D-mannitol, and the like.

Examples of suspending agents include stearyltriethanolamine, sodium lauryl sulfate, benzalkonium chloride, and the like.

The administration schedule of the present invention is suitably selected according to conditions such as the age and sex of a patient, stage of disease, presence or absence of metastasis, and medical history. For example, the combination chemotherapy of the present invention is preferably conducted according to the following schedule. During a four-week period, tegafur, gimeracil and oteracil potassium are administered for 21 consecutive days; and on the first day of the administration (first day), cisplatin is administered. This is regarded as one cycle, and one cycle or a plurality of cycles are conducted.

The target patients for the prediction method of the present invention are patients with gastric cancer, and may also be patients with gastric cancer as a primary focus and with gastric cancer that has metastasized to an organ or tissue other than the stomach.

In the present invention, the histologic type of the target patients with gastric cancer may be diffuse type or non-diffuse type, but is preferably diffuse type, the dihydropyrimidine dehydrogenase gene expression levels of which are reported to be high (Int. J. Cancer 2004; 112: 967-973).

Biological samples that can be used in measuring the expression level of dihydropyrimidine dehydrogenase gene in the present invention are not particularly limited as long as they are likely to contain cancer cells. Examples thereof include body fluid (such as blood and urine), tissues, extracts thereof, and cultures of the obtained tissues. Methods for collecting biological samples can be suitably selected according to the type of biological samples or type of cancers. The preparation of DNA, RNA, and proteins from biological samples can be conducted according to commonly known methods. As the tissues, the stomach can be mentioned in particular; however, when cancer cells have metastasized from the stomach to other organs, peritoneum, or the like, the tissues at the metastasis sites become target tissues.

Dihydropyrimidine dehydrogenase is a rate-limiting enzyme that acts at an earlier stage in the degradation pathway of uracil and thymine, and is also known as a catabolic enzyme of 5-FU. The base sequence and amino acid sequence of human dihydropyrimidine dehydrogenase gene are known (J Biol Chem. 269 (37): 23192-6 (1994)).

The prediction method of the present invention employs the expression level of dihydropyrimidine dehydrogenase gene as an index. The expression level may be that of mRNA, or that of a protein. Here, the expression level of mRNA can be measured using a probe or primer that specifically hybridizes with dihydropyrimidine dehydrogenase gene, according to known methods for measuring gene expression levels, such as Northern blotting method, quantitative or semi-quantitative PCR method (for example, RT-PCR method and real-time PCR method), and in situ hybridization method. The above expression level can be assessed by comparison with a protein/gene that is expressed at a constant level (for example, a housekeeping gene, such as β-actin, or its expressed protein) as a reference standard.

The level of protein expression can be measured by conducting a known immunological assay, such as an enzyme immunoassay, radioimmunoassay, fluoroimmunoassay, ELISA, Western blotting technique, or immunohistochemical staining assay, using an antibody that specifically recognizes dihydropyrimidine dehydrogenase.

Probes used in the methods for measuring gene expression levels, such as Northern blot technique and in situ hybridization, are designed, according to commonly known probe design methods, to specifically hybridize with a continuous base sequence of at least 15 bases to the total base length, preferably 20 bases to the total base length, more preferably 30 bases to the total base length, of the base sequence of dihydropyrimidine dehydrogenase gene; and are in the form of polynucleotides having the above-mentioned base length.

Primers and probes used in quantitative or semi-quantitative PCR method, such as RT-PCR method and real-time PCR method, can be designed, for example, in the following manner.

The primers and probes of the present invention are designed according to commonly known primer and probe design methods, to specifically hybridize with a continuous base sequence of at least 10 bases to the total base length, preferably 10 to 100 bases, more preferably 10 to 50 bases, still more preferably 10 to 35 bases of the base sequence of dihydropyrimidine dehydrogenase gene; and are in the form of polynucleotides having the above-mentioned base length. For example, primers for detecting the expression products of dihydropyrimidine dehydrogenase gene, i.e., forward and reverse primers for PCR, can be designed and synthesized from exon regions of dihydropyrimidine dehydrogenase gene. The forward and reverse primers are designed such that one is designed based on the base sequence of the upstream region of exon regions of dihydropyrimidine dehydrogenase gene (forward primer), and the other is designed based on the base sequence of the downstream region of the exon regions (reverse primer). For example, in designing dihydropyrimidine dehydrogenase gene primers based on exons 1 to 3, when the forward primer is designed based on the sequence of the exon 1 region, the reverse primer is designed based on the sequence of the downstream exon 2 region or exon 3 region. The reverse primer is designed to be complementary to the sequence of mRNA of dihydropyrimidine dehydrogenase. Further, each primer can be made using the whole or a part of the base sequence of mRNA of dihydropyrimidine dehydrogenase containing the exon regions; however, it is desirable to design each primer in consideration of the efficiency of amplification from the exon regions in PCR. More specifically, a primer of SEQ ID NO: 1 or 7 is preferred as a forward primer for detecting expression products of dihydropyrimidine dehydrogenase gene, and a primer of SEQ ID NO: 2 or 8 is preferred as a reverse primer for detecting expression products of dihydropyrimidine dehydrogenase gene. In terms of measuring only mRNA, not DNA on the genome, a primer of SEQ ID NO: 7 is particularly preferred as the forward primer, and a primer of SEQ ID NO: 8 is particularly preferred as the reverse primer.

Probes for detecting expression products of dihydropyrimidine dehydrogenase gene are not particularly limited as long as they can hybridize with a single-stranded DNA of dihydropyrimidine dehydrogenase gene that is to be amplified using the above primers by a PCR reaction. Any probes may be used as long as they have a sequence complementary to the base sequence of all exons of dihydropyrimidine dehydrogenase gene or a portion thereof, or as long as they are hybridizable under a stringent condition. More specifically, a probe of SEQ ID NO: 3 or 9 is preferred as the probe for detecting expression products of dihydropyrimidine dehydrogenase gene, and in terms of measuring only mRNA, not DNA on the genome, a probe of SEQ ID NO: 9 is particularly preferred.

The probes are not always required to be fully complementary to the base sequence of dihydropyrimidine dehydrogenase gene as long as they specifically hybridize with dihydropyrimidine dehydrogenase gene. Such polynucleotides have an identity of not less than 70%, preferably not less than 80%, more preferably not less than 90%, still more preferably not less than 95%, and still furthermore preferably not less than 98%, in the base sequence, as compared to either the polynucleotide having a continuous base sequence of preferably at least 15 bases of the base sequence of dihydropyrimidine dehydrogenase gene, or the complementary polynucleotide thereof.

In the present invention, "specific hybridization" refers to a hybridization that forms a specific hybrid and does not form a nonspecific hybrid under a stringent hybridization condition. The stringent hybridization condition can be determined according to commonly known methods, for example, based on the melting temperature (Tm) of the nucleic acid at which the hybrid is formed. A specific cleaning condition to maintain the hybridization condition is commonly about "1×SSC, 0.1% SDS, 37° C.," more strictly about "0.5×SSC, 0.1% SDS, 42° C.," and still more strictly about "0.1×SSC, 0.1% SDS, 65° C."

Because the base sequence of dihydropyrimidine dehydrogenase gene in humans is known, the probes or primers can be made by commonly known synthesis methods, for example, using a commercially available nucleotide synthesizer, based on the base sequence. The probes or primers can also be prepared by PCR method using the base sequence as a template.

Moreover, to easily detect dihydropyrimidine dehydrogenase gene, the probes or primers may be labeled with a commonly used radioactive substance, fluorescent substance, chemical luminescent substance, or enzyme.

The antibody of the present invention is not particularly limited as long as it specifically recognizes dihydropyrimidine dehydrogenase. The antibody may be either monoclonal or polyclonal; or an antibody fragment, such as Fab and F(ab')2 fragments. This antibody can be produced according to commonly known methods (for example, Current Protocols in Molecular Biology, Edit. Ausubel et al. (1987), Publish. John Wiley and Sons. Section 11.12-11.13).

In the step of predicting whether combination chemotherapy with cisplatin and a combination drug of tegafur/gimeracil/oteracil potassium should be performed, it is predicted that when the expression level of dihydropyrimidine dehydrogenase gene is higher than a predetermined cut-off point, the patient is likely to sufficiently respond to the combination chemotherapy.

The cut-off point in the present invention is varied depending on conditions such as the subjects to be measured and the type of measurement methods, and is therefore required to be predetermined according to the conditions. Because the cut-off point is varied according to the subjects to be measured (the number, age, sex, body weight, health state, and disease state of patients), measurement methods (regarding which expression product, either gene or protein, is used for measurement), measurement conditions (for example, sequences of primers and probes in measuring gene expression products (mRNA), the type of label, the type and sensitivity of an antibody in the case where the expression product is a protein, and the like), statistical techniques, or other conditions, the present invention widely encompasses inventions using an arbitrary cut-off point that can be varied depending on these conditions, and is not limited to a particular value. Here, the cut-off point can be determined from the previously measured expression level of dihydropyrimidine dehydrogenase gene by using various statistical analysis techniques. Examples thereof include the average or median value of the expression level of dihydropyrimidine dehydrogenase gene in the TS-1/cisplatin combination group or in patients undergoing combination chemotherapy with 5-FU/cisplatin; a value in which the hazard ratio (ratio of mortality rates at a certain moment) of the TS-1/cisplatin combination group to the 5-FU/cisplatin combination group is minimal; a value in which the difference in 2-year survival rate between the TS-1/cisplatin combination group and the 5-FU/cisplatin combination group is maximal; a value in which the hazard ratio of the TS-1/cisplatin combination group to the 5-FU/cisplatin combination group is not greater than a certain value (for example, the hazard ratio is not greater than 0.7 (the risk of death in the TS-1/cisplatin combination group decreases by 30% or more as compared to the 5-FU/cisplatin combination group); and a value in which P-value of the log-rank test for the survival time of the 5-FU/cisplatin combination group and the TS-1/cisplatin combination group is minimal or less than a certain level (for example, a value in which the P-value is less than 0.1, or less than 0.05).

As a result, the cut-off point (a ratio to beta actin) for the expression level of dihydropyrimidine dehydrogenase gene in this combination chemotherapy is, for example, in the real-time PCR method, preferably $0.35 \times 10^{-3}$ to $4.33 \times 10^{-3}$, more preferably $0.83 \times 10^{-3}$ to $2.23 \times 10^{-3}$. Further, in cases where the real-time PCR method using primers and probes of SEQ ID NOs: 1-6 is carried out, the cut-off point is preferably $0.83 \times 10^{-3}$ to $2.33 \times 10^{-3}$, more preferably $0.96 \times 10^{-3}$ to $1.49 \times 10^{-3}$, particularly preferably $1.49 \times 10^{-3}$. In cases where the real-time PCR method using primers and probes of SEQ ID NOs: 7-12 is carried out, the cut-off point is preferably $0.35 \times 10^{-3}$ to $4.33 \times 10^{-3}$, more preferably $0.35 \times 10^{-3}$ to $1.86 \times 10^{-3}$, particularly preferably $1.06 \times 10^{-3}$ to $1.86 \times 10^{-3}$. The ratio of cases with dihydropyrimidine dehydrogenase gene expression levels lower than these cut-off points is 8.1% to 39.4% with the primers and probes of SEQ ID NOs: 1-6; and is 25.0% to 92.9% with the primers and probes of SEQ ID NOs: 7-12. Based on these ratios, the cut-off point can be determined.

The primer pair of the present invention for measuring the expression level of dihydropyrimidine dehydrogenase comprises a forward primer of SEQ ID NO: 1 and a reverse primer of SEQ ID NO: 2, or a forward primer of SEQ ID NO: 7 and a reverse primer of SEQ ID NO: 8. In terms of measuring only mRNA, not DNA on the genome, the primer pair preferably comprises the forward primer of SEQ ID NO: 7 and the reverse primer of SEQ ID NO: 8. The kit of the present invention for measuring the expression level of dihydropyrimidine dehydrogenase comprises the above-described primer pair, preferably further comprises a probe of SEQ ID NO: 3 or 9, and in terms of measuring only mRNA, not DNA on the genome, the kit particularly preferably comprises a probe of SEQ ID NO: 9.

The primer pair and the kit of the present invention for measuring the expression level of dihydropyrimidine dehydrogenase enable the accurate measurement of expression level of dihydropyrimidine dehydrogenase and can be used for predicting the therapeutic effect of chemotherapy comprising a 5-FU based antitumor agent. The chemotherapy comprising a 5-FU based antitumor agent is not particularly limited as long as it comprises 5-FU or a derivative thereof. Examples thereof include chemotherapy comprising 5-FU, a combination drug of tegafur/uracil, or a combination drug of tegafur/gimeracil/oteracil potassium. Of these, chemotherapy comprising a combination drug of tegafur/gimeracil/oteracil potassium is preferred and combination chemotherapy with cisplatin and a combination drug of tegafur/gimeracil/oteracil potassium is particularly preferred. The target cancer for prediction of therapeutic effects is not particularly limited, but is preferably gastric cancer, colon/rectal cancer, head and neck cancer, lung cancer, breast cancer, pancreatic cancer, and biliary tract cancer; and is particularly preferably gastric cancer.

EXAMPLES

Examples are given below to illustrate the present invention in more detail; however, it goes without saying that the present invention is not limited to these Examples.

Example 1

Measurement of Expression Level of Dihydropyrimidine Dehydrogenase Gene

A biomarker study (measurement of the protein expression level of dihydropyrimidine dehydrogenase gene) was conducted in clinical trials of TS-1/cisplatin combination therapy and 5-FU/cisplatin combination therapy for previously untreated Caucasian advanced gastric cancer patients.

The TS-1/cisplatin combination therapy was conducted by way of oral administration of TS-1 in a tegafur amount of 25 mg/m² (per body surface area) to a fasted patient twice a day for 21 consecutive days, followed by a 7-day withdrawal. On the first day (Day 1) of TS-1 administration, 75 mg/m² of cisplatin was administered by intravenous injection over 1 to 3 hours after the first administration of TS-1. The 4-week (28-day) administration was regarded as one cycle, and the administrations were repeated up to 6 cycles.

The 5-FU/cisplatin combination therapy was conducted by way of intravenous administration of 5-FU in an amount of 1000 mg/m$^2$/24 hours for 5 consecutive days, followed by a 23-day withdrawal. On the first day (Day 1) of 5-FU administration, 100 mg/m$^2$ of cisplatin was administered by intravenous injection over 1 to 3 hours before the administration of 5-FU. The 4-week (28-day) administration was regarded as one cycle, and the administrations were repeated up to 6 cycles.

The survival period was defined as the period from the date of randomization to the date of death. For the patients who have not been confirmed dead upon the analysis or the surviving patients, the observation was stopped at the latest assessment.

The expression level of dihydropyrimidine dehydrogenase gene was quantified as a ratio to beta actin according to TaqMan® real time PCR, using total RNA extracted from formalin-fixed paraffin-embedded sections of tumor tissues of surgical or biopsy specimens obtained prior to chemotherapy. The primers and probe of SEQ ID NO: 1 to SEQ ID NO: 3 identified below were used as the primers and probe for measuring expression level of dihydropyrimidine dehydrogenase gene. The primers and probe of SEQ ID NO: 4 to SEQ ID NO: 6 identified below were used as the primers and probe for measuring the expression level of beta actin gene.

TABLE 1

| Gene name | Forward primer | Reverse primer | TaqMan MGB probe |
|---|---|---|---|
| Dihydropyrimidine dehydrogenase | TCTGGCTACC AGGCTATACA GTTT (SEQ ID NO: 1) | CAGCCTGTAC AAGTGTCGGT TAT (SEQ ID NO: 2) | AAACCCACCT GCCCAC (SEQ ID NO: 3) |
| Beta actin | AAGGCCAACC GCGAGAAG (SEQ ID NO: 4) | ATAGCAACGT ACATGGCTGG G (SEQ ID NO: 5) | ACCCAGATCA TGTTT (SEQ ID NO: 6) |

In addition to the primers and probes shown in Table 1 above, various forward primers, reverse primers, and probes can be designed based on the open reading frame of known dihydropyrimidine dehydrogenase gene sequence. The change in the sequences of primers or probes, type of label, etc., may slightly change the cut-off point; however, they have no substantial influence on the effect of the present invention, i.e., the effect that enables the prediction of whether a patient sufficiently responds to chemotherapy with cisplatin and a combination drug of tegafur/gimeracil/oteracil potassium.

Example 2

Calculation of Cut-Off Points

Cut-off points were determined from the expression level of dihydropyrimidine dehydrogenase gene in each patient, which was measured in Example 1, according to the following statistical analysis techniques.

(1) A cut-off point in which the hazard ratio of TS-1/cisplatin combination group with respect to 5-FU/cisplatin combination group was minimal was calculated. The calculated cut-off point was 1.49×10$^{-3}$.

(2) A cut-off point in which the difference in 2-year survival rate between TS-1/cisplatin combination group and 5-FU/cisplatin combination group was maximal was calculated. The calculated cut-off point was 0.96×10$^{-3}$.

(3) A cut-off point in which the hazard ratio of TS-1/cisplatin combination group with respect to 5-FU/cisplatin combination group was 0.7 or less was calculated. The calculated cut-off point was 0.83×10$^{-3}$ to 2.23×10$^{-3}$.

The cut-off point denotes a ratio of the expression level of dihydropyrimidine dehydrogenase gene to beta actin.

Example 3

Therapeutic effects of combination therapy in patients selected according to the index, i.e., dihydropyrimidine dehydrogenase The hazard ratios and 2-year survival rates of the groups with high expression levels of dihydropyrimidine dehydrogenase were calculated using the cut-off point values calculated in Example 2. Tables 2 to 5 show the results.

TABLE 2

Cut-off point value: 0.89 × 10$^{-3}$ (lower limit of cut-off point in which the hazard ratio is 0.7 or less)

| Subject | Number of cases | Hazard ratio | 2-year survival rate (%) | Relative rate of cases (%) |
|---|---|---|---|---|
| TS-1/cisplatin combination group | 52 | 0.68 | 13.4 | 91.9 |
| 5-FU/cisplatin combination group | 39 | — | 0.0 | |

TABLE 3

Cut-off point value: 0.96 × 10$^{-3}$ (maximal difference in 2-year survival rate)

| Subject | Number of cases | Hazard ratio | 2-year survival rate (%) | Relative rate of cases (%) |
|---|---|---|---|---|
| TS-1/cisplatin combination group | 51 | 0.66 | 13.7 | 89.9 |
| 5-FU/cisplatin combination group | 38 | — | 0.0 | |

TABLE 4

Cut-off point value: $1.49 \times 10^{-3}$ (minimal hazard ratio)

| Subject | Number of cases | Hazard ratio | 2-year survival rate (%) | Relative rate of cases (%) |
|---|---|---|---|---|
| TS-1/cisplatin combination group | 46 | 0.65 | 12.8 | 81.8 |
| 5-FU/cisplatin combination group | 35 | — | 0.0 | |

TABLE 5

Cut-off point value: $2.23 \times 10^{-3}$
(upper limit of cut-off point in which the hazard ratio is 0.7 or less)

| Subject | Number of cases | Hazard ratio | 2-year survival rate (%) | Relative rate of cases (%) |
|---|---|---|---|---|
| TS-1/cisplatin combination group | 33 | 0.69 | 11.8 | 60.6 |
| 5-FU/cisplatin combination group | 27 | — | 0.0 | |

The patients who have high expression levels of dihydropyrimidine dehydrogenase gene in the tumor tissues had a significantly low hazard ratio of the TS-1/cisplatin combination therapy with respect to 5-FU/cisplatin combination therapy, namely ranging from 0.65 to 0.69, demonstrating high life-prolongation effects.

Example 4

Measurement of Expression Level of Dihydropyrimidine Dehydrogenase Gene

Measurement of expression level of dihydropyrimidine dehydrogenase gene was conducted in the same manner as in Example 1 with substantially the same specimen, using the primers and probes of SEQ ID NO: 7 to SEQ ID NO: 12 shown below instead of the primers and probes used in Example 1. The primers and probes of SEQ ID NO: 7 to SEQ ID NO: 12 are designed so that the sequences are set in the splicing sites, thereby measuring only mRNA (rather than DNA on the genome).

TABLE 6

| Gene name | Forward primer | Reverse primer | TaqMan MGB probe |
|---|---|---|---|
| Dihydropyrimidine dehydrogenase | TTCAGTTTCT CCATAGTGGT GCTT (SEQ ID NO: 7) | CACAGTGAAA TCCTGATTCT GAATG (SEQ ID NO: 8) | TCCTCCAGGT ATGCAGTG (SEQ ID NO: 9) |
| Beta actin | CCTCGCCTTT GCCGATC (SEQ ID NO: 10) | CGAGCGCGGC GATATCA (SEQ ID NO: 11) | CGCCAGCTCA CCATG (SEQ ID NO: 12) |

Example 5

Calculation of Cut-Off Points

Cut-off points were determined from the expression level of dihydropyrimidine dehydrogenase gene in each patient, which was measured in Example 4, according to the following statistical analysis techniques.

(1) A cut off point in which the hazard ratio of TS-1/cisplatin combination group with respect to 5-FU/cisplatin combination group was 0.7 or less was calculated. The calculated cut-off point was $0.35 \times 10^{-3}$ to $4.33 \times 10^{-3}$.

(2) A cut off point in which the P-value of the log-rank test was less than 0.05 in the survival periods of the 5-FU/cisplatin combination group and the TS-1/cisplatin combination group was calculated. The calculated cut-off point was $1.06 \times 10^{-3}$ to $1.86 \times 10^{-3}$.

The cut-off point denotes a ratio of the expression level of dihydropyrimidine dehydrogenase gene to beta actin.

Example 6

Therapeutic effects of combination therapy in patients selected according to the index, i.e., dihydropyrimidine dehydrogenase The hazard ratio and 2-year survival rate of the groups with high expression levels of dihydropyrimidine dehydrogenase were calculated using the cut-off point values calculated in Example 5. Tables 7 to 9 show the results.

TABLE 7

Cut-off point value: $0.35 \times 10^{-3}$ (lower limit of cut-off point in which the hazard ratio is 0.7 or less)

| Subject | Number of cases | Hazard ratio | 2-year survival rate (%) | Relative rate of cases (%) |
|---|---|---|---|---|
| TS-1/cisplatin combination group | 43 | 0.70 | 12.1 | 90.5 |
| 5-FU/cisplatin combination group | 33 | — | 0.0 | |

TABLE 8

Cut-off point value: $1.06 \times 10^{-3}$ (lower limit of cut-off point in which the P-value of the log-rank test is less than 0.05)

| Subject | Number of cases | Hazard ratio | 2-year survival rate (%) | Relative rate of cases (%) |
|---|---|---|---|---|
| TS-1/cisplatin combination group | 24 | 0.45 | 17.6 | 47.6 |
| 5-FU/cisplatin combination group | 16 | — | 0.0 | |

TABLE 9

Cut-off point value: $1.86 \times 10^{-3}$ (upper limit of cut-off point in which the P-value of the log-rank test is less than 0.05)

| Subject | Number of cases | Hazard ratio | 2-year survival rate (%) | Relative rate of cases (%) |
|---|---|---|---|---|
| TS-1/cisplatin combination group | 13 | 0.39 | 17.9 | 25.0 |
| 5-FU/cisplatin combination group | 8 | — | 0.0 | |

The patients who have high expression levels of dihydropyrimidine dehydrogenase gene in the tumor tissues had a significantly low hazard ratio of the TS-1/cisplatin combination therapy with respect to 5-FU/cisplatin combination therapy, namely ranging from 0.39 to 0.70, demonstrating high life-prolongation effects.

As shown above, it is evident that selecting a gastric cancer patient according to the expression level of dihydropyrimidine dehydrogenase gene makes it possible to ensure a high life-prolongation effect of the TS-1/cisplatin combination therapy, compared with the 5-FU/cisplatin combination therapy that does not contain a dihydropyrimidine dehydrogenase inhibitor.

What is claimed is:

1. A therapeutic method for treating a patient with gastric cancer, comprising:
    measuring an expression level of dihydropyrimidine dehydrogenase gene in a biological sample that is obtained from the patient;
    determining whether the expression level of dihydropyrimidine dehydrogenase gene in the biological sample is higher than a corresponding cut-off point;
    administering a combination chemotherapy of cisplatin and a combination drug of tegafur/gimeracil/oteracil potassium to the patient if the said expression level is higher than the said predetermined cut-off point,
    wherein the predetermined cut-off point is a value selected from the following:
    [1] an average or median value of the expression level of dihydropyrimidine dehydrogenase gene in the TS-1/cisplatin combination group or in patients undergoing combination chemotherapy with 5-FU/cisplatin;
    [2] a value in which the hazard ratio of the TS-1/cisplatin combination group to the 5-FU/cisplatin combination group is minimal;
    [3] a value in which the difference in 2-year survival rate between the TS-1/cisplatin combination group and the 5-FU/cisplatin combination group is maximal;
    [4] a value in which the hazard ratio of the TS-1/cisplatin combination group to the 5-FU/cisplatin combination group is not greater than a certain value; and
    [5] a value in which P-value of the log-rank test for the survival time of the 5-FU/cisplatin combination group and the TS-1/cisplatin combination group is minimal or less than a certain level.

2. The method according to claim 1, wherein the molar ratio of respective active ingredients in the combination drug of tegafur/gimeracil/oteracil potassium, i.e., the ratio of tegafur:gimeracil:oteracil potassium, is 1:0.4:1.

3. A therapeutic method for treating a patient with gastric cancer, comprising:
    measuring an expression level of dihydropyrimidine dehydrogenase gene in a biological sample that is obtained from the patient;
    determining whether the expression level of dihydropyrimidine dehydrogenase gene in the biological sample is higher than a corresponding cut-off point;
    administering a combination chemotherapy of cisplatin and a combination drug of tegafur/gimeracil/oteracil potassium to the patient if the said expression level is higher than the said predetermined cut-off point,
    wherein the predetermined cut-off point is a ratio of the expression level of dihydropyrimidine dehydrogenase gene to beta actin gene measured by the real-time PCR method and is a value selected from the following:
    [1] $0.83 \times 10^{-3}$ to $2.33 \times 10^{-3}$ when the expression level of dihydropyrimidine dehydrogenase is measured using primers of SEQ ID NO: 1 and SEQ ID NO: 2 and a probe of SEQ ID NO: 3, and the expression level of beta actin gene is measured using primers of SEQ ID NO: 4 and SEQ ID NO: 5, and a probe of SEQ ID NO: 6; and
    [2] $0.35 \times 10^{-3}$ to $4.33 \times 10^{-3}$ when the expression level of dihydropyrimidine dehydrogenase is measured using primers of SEQ ID NO: 7 and SEQ ID NO: 8 and a probe of SEQ ID NO: 9, and the expression level of beta actin gene is measured using primers of SEQ ID NO: 10 and SEQ ID NO: 11, and a probe of SEQ ID NO: 12.

4. The method according to claim 3, wherein the molar ratio of respective active ingredients in the combination drug of tegafur/gimeracil/oteracil potassium, i.e., the ratio of tegafur:gimeracil:oteracil potassium, is 1:0.4:1.

5. A therapeutic method for treating a patient with gastric cancer, comprising:
    measuring an expression level of dihydropyrimidine dehydrogenase gene in a biological sample that is obtained from the patient;
    determining whether the expression level of dihydropyrimidine dehydrogenase gene in the biological sample is higher than a corresponding cut-off point;
    administering a combination chemotherapy of cisplatin and a combination drug of tegafur/gimeracil/oteracil potassium to the patient if the said expression level is higher than the said predetermined cut-off point,
    wherein the predetermined cut-off point is a ratio of the expression level of dihydropyrimidine dehydrogenase gene to beta actin gene measured by a real-time PCR method and is a value selected from the following:
    [1] $0.96 \times 10^{-3}$ to $1.49 \times 10^{-3}$ when the expression level of dihydropyrimidine dehydrogenase is measured using primers of SEQ ID NO: 1 and SEQ ID NO: 2 and a probe of SEQ ID NO: 3, and the expression level of beta actin gene is measured using primers of SEQ ID NO: 4 and SEQ ID NO: 5, and a probe of SEQ ID NO: 6; and
    [2] $0.35 \times 10^{-3}$ to $1.86 \times 10^{-3}$ when the expression level of dihydropyrimidine dehydrogenase is measured using primers of SEQ ID NO: 7 and SEQ ID NO: 8 and a probe of SEQ ID NO: 9, and the expression level of beta actin gene is measured using primers of SEQ ID NO: 10 and SEQ ID NO: 11, and a probe of SEQ ID NO: 12.

6. The method according to claim 5, wherein the molar ratio of respective active ingredients in the combination drug of tegafur/gimeracil/oteracil potassium, i.e., the ratio of tegafur:gimeracil:oteracil potassium, is 1:0.4:1.

* * * * *

```
SEQUENCE LISTING

<160> NUMBER OF SEQ ID NOS: 12

<210> SEQ ID NO 1
<211> LENGTH: 24
<212> TYPE: DNA
<213> ORGANISM: Artificial
<220> FEATURE:
<223> OTHER INFORMATION: Forward Primer

<400> SEQUENCE: 1
tctggctacc aggctataca gttt                                              24

<210> SEQ ID NO 2
<211> LENGTH: 23
<212> TYPE: DNA
<213> ORGANISM: Artificial
<220> FEATURE:
<223> OTHER INFORMATION: Reverse Primer

<400> SEQUENCE: 2
cagcctgtac aagtgtcggt tat                                               23

<210> SEQ ID NO 3
<211> LENGTH: 16
<212> TYPE: DNA
<213> ORGANISM: Artificial
<220> FEATURE:
<223> OTHER INFORMATION: Taqman MGB Probe

<400> SEQUENCE: 3
aaacccacct gcccac                                                       16

<210> SEQ ID NO 4
<211> LENGTH: 18
<212> TYPE: DNA
<213> ORGANISM: Artificial
<220> FEATURE:
<223> OTHER INFORMATION: Forward Primer

<400> SEQUENCE: 4
```

-continued aaggccaacc gcgagaag                                                18

<210> SEQ ID NO 5
<211> LENGTH: 21
<212> TYPE: DNA
<213> ORGANISM: Artificial
<220> FEATURE:
<223> OTHER INFORMATION: Reverse Primer

<400> SEQUENCE: 5
atagcaacgt acatggctgg g                                            21

<210> SEQ ID NO 6
<211> LENGTH: 15
<212> TYPE: DNA
<213> ORGANISM: Artificial
<220> FEATURE:
<223> OTHER INFORMATION: Taqman MGB Probe

<400> SEQUENCE: 6
acccagatca tgttt                                                   15

<210> SEQ ID NO 7
<211> LENGTH: 24
<212> TYPE: DNA
<213> ORGANISM: Artificial
<220> FEATURE:
<223> OTHER INFORMATION: Forward Primer

<400> SEQUENCE: 7
ttcagtttct ccatagtggt gctt                                         24

<210> SEQ ID NO 8
<211> LENGTH: 25
<212> TYPE: DNA
<213> ORGANISM: Artificial Sequence
<220> FEATURE:
<223> OTHER INFORMATION: Reverse Primer

<400> SEQUENCE: 8
cacagtgaaa tcctgattct gaatg                                        25

<210> SEQ ID NO 9
<211> LENGTH: 18
<212> TYPE: DNA
<213> ORGANISM: Artificial
<220> FEATURE:
<223> OTHER INFORMATION: Taqman MGB Probe

<400> SEQUENCE: 9
tcctccaggt atgcagtg                                                18

<210> SEQ ID NO 10
<211> LENGTH: 17
<212> TYPE: DNA
<213> ORGANISM: Artificial
<220> FEATURE:
<223> OTHER INFORMATION: Forward Primer

<400> SEQUENCE: 10
cctcgccttt gccgatc                                                 17

<210> SEQ ID NO 11
<211> LENGTH: 17
<212> TYPE: DNA
<213> ORGANISM: Artificial
<220> FEATURE:

```
<223> OTHER INFORMATION: Reverse Primer

<400> SEQUENCE: 11
cgagcgcggc gatatca                                                  17

<210> SEQ ID NO 12
<211> LENGTH: 15
<212> TYPE: DNA
<213> ORGANISM: Artificial Sequence
<220> FEATURE:
<223> OTHER INFORMATION: Taqman MGB probe

<400> SEQUENCE: 12
cgccagctca ccatg                                                    15
```